(12) United States Patent
Ielpo et al.

(10) Patent No.: US 6,635,028 B1
(45) Date of Patent: Oct. 21, 2003

(54) SURGICAL DEVICE FOR THE IRRIGATION AND THE SUCTION OF A PHYSIOLOGICAL SOLUTION

(75) Inventors: Filippo Ielpo, Rome (IT); Dante Pocci, Rome (IT); Maurizio Podrini, Rome (IT)

(73) Assignee: Centro Sviluppo Materiali S.p.A., Rome (IT)

( * ) Notice: Subject to any disclaimer, the term of this patent is extended or adjusted under 35 U.S.C. 154(b) by 0 days.

(21) Appl. No.: 09/581,568
(22) PCT Filed: Dec. 16, 1998
(86) PCT No.: PCT/IT98/00365
§ 371 (c)(1), (2), (4) Date: Jan. 17, 2001
(87) PCT Pub. No.: WO99/30758
PCT Pub. Date: Jun. 24, 1999

(30) Foreign Application Priority Data

Dec. 16, 1997 (IT) .......................... RM97A0781

(51) Int. Cl.⁷ .......................... A61M 1/00; A61M 7/00; B67C 3/16
(52) U.S. Cl. .......................... 604/27; 604/319; 137/205
(58) Field of Search .......................... 604/119, 540, 604/319, 27; 215/246; 137/205

(56) References Cited

U.S. PATENT DOCUMENTS

| 4,402,687 A | * | 9/1983 | Denty et al. .......... 215/246 |
|---|---|---|---|
| 4,516,973 A | | 5/1985 | Telang |
| 4,522,623 A | * | 6/1985 | Lauterjung .......... 137/205 |
| 4,913,698 A | | 4/1990 | Ito et al. |
| 5,368,569 A | | 11/1994 | Sanese |
| 5,382,244 A | * | 1/1995 | Telang .......... 604/119 |

FOREIGN PATENT DOCUMENTS

| EP | 0 278 188 A2 | 8/1988 |
|---|---|---|
| EP | 0 676 214 A1 | 10/1995 |
| WO | WO 94/27659 A1 | 12/1994 |

* cited by examiner

Primary Examiner—Brian L. Casler
Assistant Examiner—Roz Ghafoorian
(74) Attorney, Agent, or Firm—Browdy and Neimark

(57) ABSTRACT

The surgical device (1) claimed is of simple construction. It includes a terminal element (4) of irrigation and suction, a propelling system (2) of the physiological solution having a rigid container (22) housing a flexible bag (M) and having a sealed lid (25) and a feed opening (32) that can be connected to a high pressure source (3) of propellant fluid, a fitting element (33), removably sealed through the rigid walls (25) of the container (22), having a through hole (38) extended between an outer joint (36), to connect a delivery duct (5) and an inner joint (37), a piercing delivery element (40, 41) projecting inside the container (22) from the inner joint (37) has a fissured nose (41) suited to pierce a flexible bag (M) once the lid (25) is sealed.

11 Claims, 4 Drawing Sheets

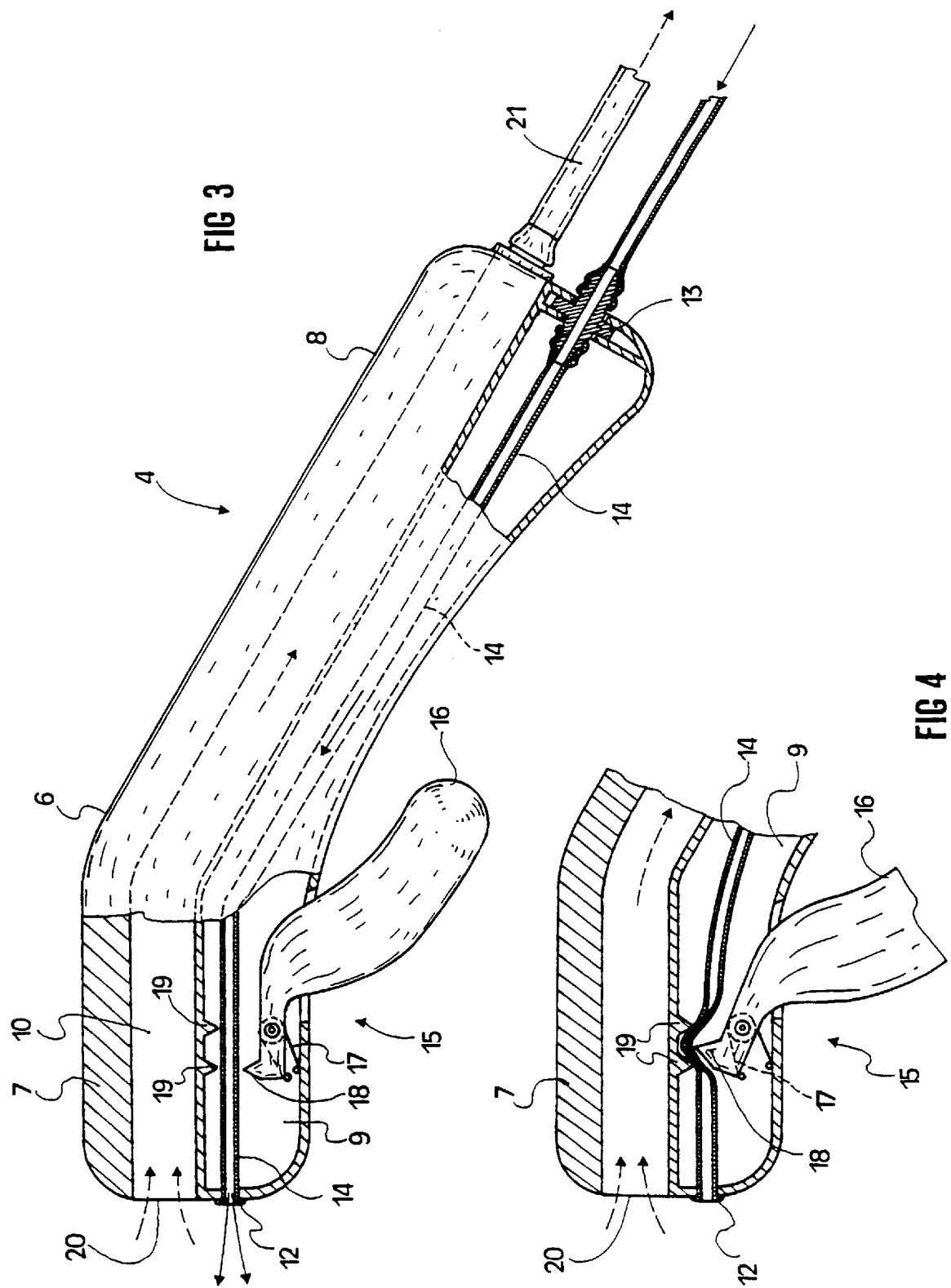

SURGICAL DEVICE FOR THE IRRIGATION AND THE SUCTION OF A PHYSIOLOGICAL SOLUTION

CROSS REFERENCE TO RELATED APPLICATION

The present application is the national stage under 35 U.S.C. 371 of PCT/IT98/00365, filed Dec. 16, 1998

BACKGROUND OF THE INVENTION

1. Technical Field of the Invention

The present invention relates to a surgical device for the irrigation and the suction of a physiological solution extracted from a flexible bag that, in its most general embodiment, comprises a terminal element of irrigation and suction, a propelling system of the physiological solution, at least one delivery duct connecting the propelling system to the terminal element, wherein the propelling system comprises: a rigid wall container, apt to house the flexible bag, having an access side, a sealed lid, a feed openig connectable to a high pressure source of propellant fluid; a fitting element, removably sealed through the lid of the container, having a through hole extended between an outer joint, for the connection. of said delivery duct and an inner joint projecting inside the container; and a delivery element projecting inside the container from said inner joint.

2. Prior Art

Devices of the aforementioned type are diffusely used in various kinds of surgery. They have the task of maintaining clean and disinfected the area undergoing surgery with the irrigation of a physiological solution. In the same context an excess of fluids gathers, caused for instance by the same physiological solution or by organic fluids like blood or the like.

Utilising the same terminal element of irrigation, this excess of fluids is removed by a localised suction.

This kind of device is known fcm the U.S. Pat. No. 4,913,698 (Ito et al.) and from the International Application No. Publ. WO/94/27695 (Guignard).

These irrigation devices must satisfy some main requirements. One of those consists in the fact that the physiological solution must continuously be maintained in perfectly aseptic conditions despite, for instance, the protracting of the surgery or the replacement of the flexible bag containing the solution.

Another requirement is determined ty the device reliability, necessarily the utmost possible, and for a duration of the surgery a priori indeterminable.

In fact, the physiological solution supply cannot fail but for the shortest possible instants, due i.e. to the aforementioned bag replacement.

To ensure maximum asepsis, once surgery has ended all components that inside the device are wet by the solution are, replaced by corresponding new or sterylised aseptic components.

Every single replaced component must therefore ensure the utmost reliability. It is hence apparent how an increase in number and complexity of components to be replaced must unavoidably be matched by a stsricter and more expensive quality control of each single component.

OBJECT AND SUMMARY OF THE INVENTION

Therefore, the need arises of a simplification in the device construction, and especially of reducing the, number of components subject to replacement.

The technical problem underlying the present invention is that of providing a surgical cevice for the irrigation and the suction capable to overcome the drawbacks mentioned with reference to the known art, satisfying in the meantime the above mentioned need.

This problem is solved by a surgical device as specified above, characteised in that said delivery is element is a piercing delivery element having a fissured nose apt to pierce the flexible bag.

The main advantage of the surgical device according to the present invention lies in the fact of entailing the replacement of only a very limited number of parts for each surgery.

BRIEF DESCRIPTION OF THE DRAWINGS

The present invention shall be disclosed hereinafter according to one of its preferred embodiments, given by way of explanation and not for limiting purposes. Reference to figures of the annexed drawings will be made, wherein:

FIG. 3 shows an elevational and partial sectional view of another component of the surgical device in FIG. 1;

FIG. 4 shows an elevational and sectional view of a detail of the component in FIG. 3.

DETAILED DESCRIPTION OF THE PREFERRED EMBODIMENT(S) OF THE INVENTION

Figure 1:
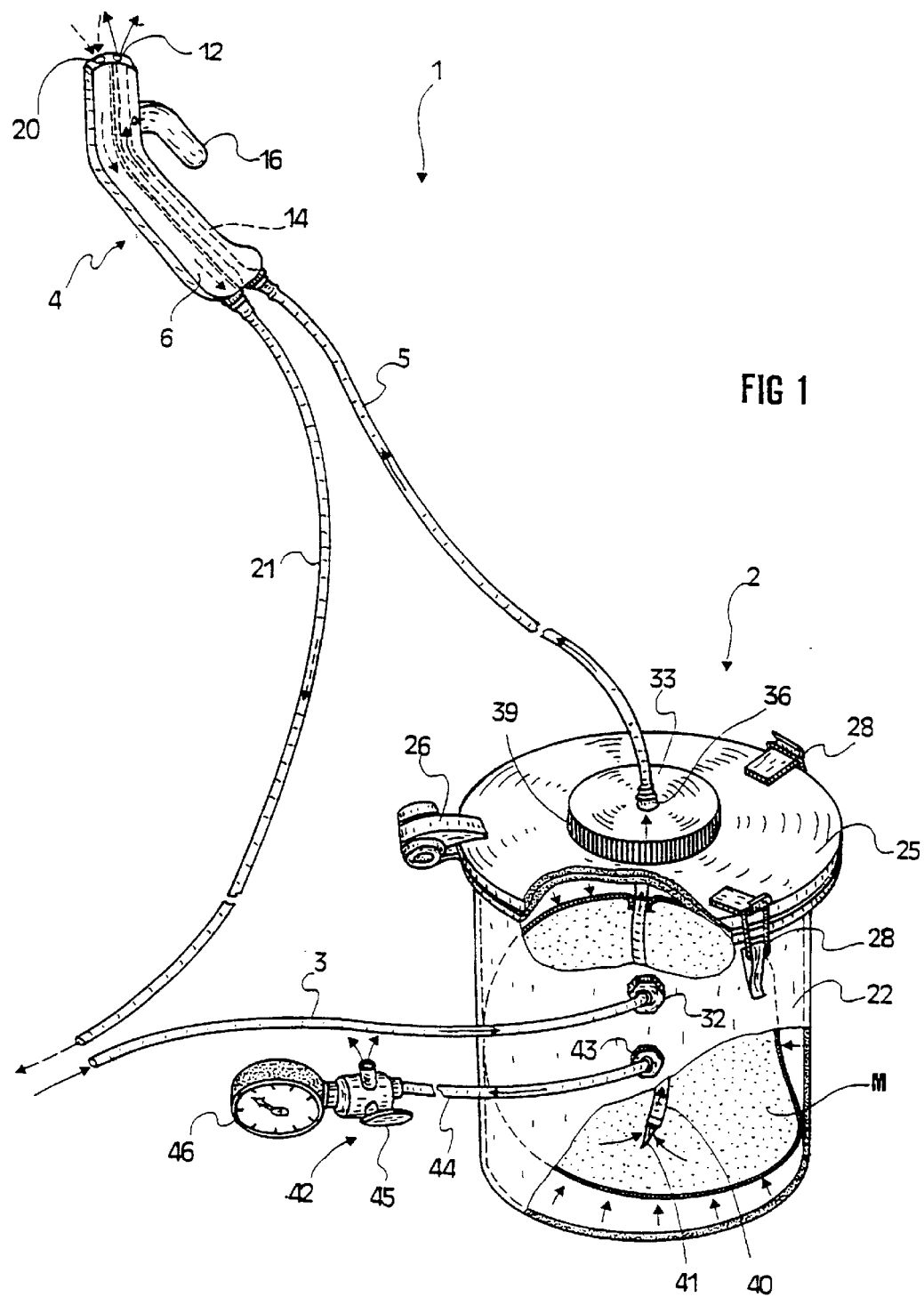
FIG. 1 shows a partial sectional perspective view of a surgical device according to the pesent invention.
Figure 2:
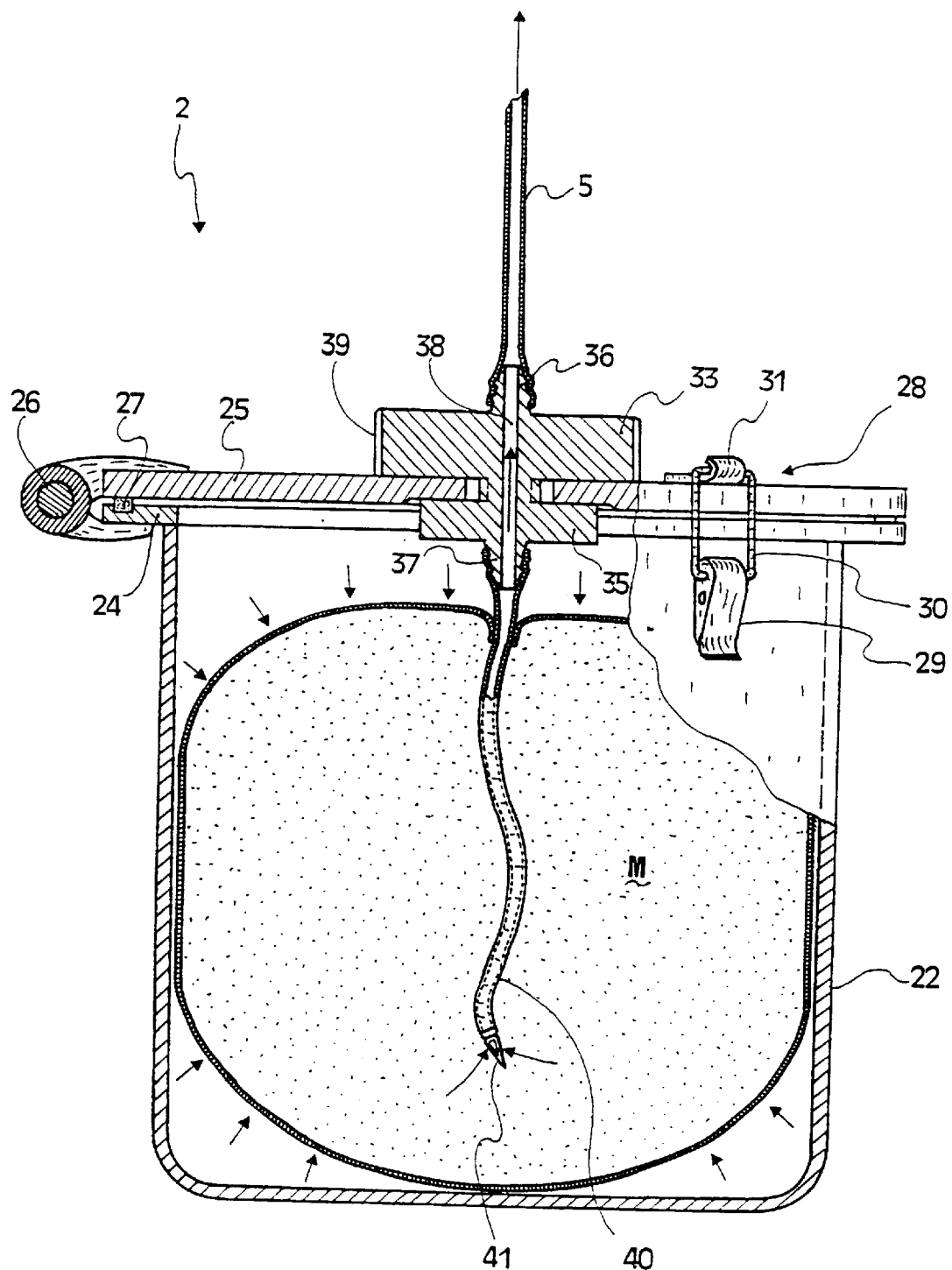
FIG. 2 shows an elevational and sectional view of a component of the surgical device in FIG. 1.
Figure 5:
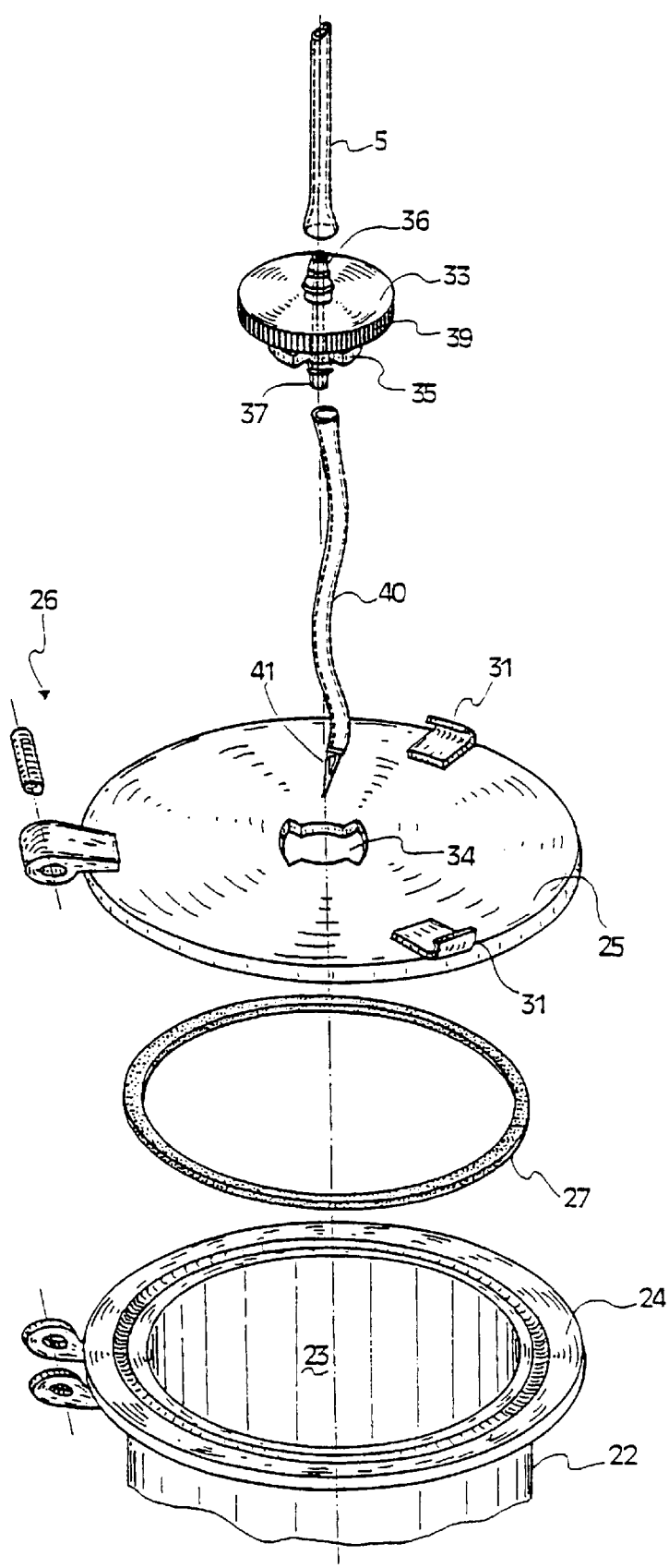
FIG. 5 shows a perspective and exploded view of a detail in FIG. 2 component.

With particular reference to FIG. 1, a surgical device of irrigation and suction is indicated 1 as a whole. It is of the type utilised to irrigate an area undergoing surgery with a physiological solution having the function of maintaining the wound clean and disinfected. Moreover, it is utilised to suck up fluids in excess from said area.

With regard to this, surgical device 1 comprises a propelling system 2 of the physiological solution connected to a high pressure source of propellant fluid.

The high pressure source is represented by a high pressure duct 3 in turn connectible with the high pressure air system usually available in an operating room. In this case the propellant fluid is air supplied in pressure.

In absence of such system any other source whatsoever can be utilised, as for instance a pressurised gas bottle or an hydraulic circuit in pressure.

The device further comprises a substantially gunshaped terminal element 4 of irrigation and suction and a flexible delivery duct, i.e. a delivery hose 5 connecting the propelling system 2 to the terminal element 4.

The gun-shaped terminal element 4 comprises a hollow body 6 which is elongated and having an essentially opened V-shape, defining an end portion 7, suited to be drawn to the area undergoing surgery, and a handle-shaped portion 8. End portion 7 and handle portion 8 are bent with respect to each other of about 150°

Inside the hollow body 6, an irrigation duct 9 and a suction duct 10 are obtained lengthwise. They are adjacent and separated by a sect 11.

The irrigation duct 9, placed correspondingly to the intrados of the hollow body 6, presents at respective ends a nozzle 12, into the end portion 7, and a bilateral joint 13 of twin cone type on handle portion 8.

The bilateral joint 13 is of the kind suitable to be engaged in lock-joint by flexible and elastic tubes of plastic material. Externally to hollow body 6, the joint 13 is connected to the delivery hose 5.

Inside the irrigation duct 7, between the nozzle 12 and the mount 13, a flexible and elastically deformable tubule 14 is extended, forming the extension of the delivery hose 5 into the terminal element 4.

The device comprises checking means 15 of the physiological solution flow that presents a trigger 16, pivotted onto hollow body 6 at its end portion, apt to be easily operated by the operator handing the terminal element 4 using gloves or the like.

The Trigger 16 is driven in a checking position by a torsion spring 17 and has a pointed end 18 apt to throttle the tubule 15 cooperating with a pair of juttings 19 of the sect 11 into the irrigation duct 9.

The suction duct 10 has a suction mouth 20 ending into the end portion 7, placed adjacently to the nozzle 12, and it is in turn connected to a flexible suction duct 21, i.e. a suction hose, that can be connected to a vacuum line usually available in an operating room.

In absence of such system it is possible to utilise for example an aspirator.

The suction through the mouth 20 is continuous, essentially depending from the distance whereto the terminal element 4 is placed from the area undergoing surgery.

Otherwise, the suction can be stopped providing an adjusting valve, of the usual kind and not shown, on the suction duct 21.

Instead, the irrigation is usually deactivated and can be activated by pressing the trigger 16 that is then recalled in its throttling position by the spring 17.

The propelling system 2 comprises a cylindrical container 22 with rigid walls having, on its top side, an access side 23 delimited by a circular rim 24.

The container 22 further comprises a sealed lid 25, constituting one of said rigid walls delimiting the container 22, rotatably connected to the circular rim 24 by a hinge 26.

The lid 25 having, on internal face thereof and in proximity of the rim, a grommet 27 wherewith the circular rim 24 cooperates.

The container 22 further comprises blocking and sealing means 28 of the locking lever kind, each comprising a lever 29, pivotted onto the container 22 at the rim 24, whereon a docking ring 30 is assembled, apt to be associated to a tooth 31 on the lid 25.

The container 22 further comprises a first feed opening 32, opened through the rigid walls of the container 22, that can be connected to the high pressure duct 3. Thus, once the lid 25 is sealed, it is possible to increase the internal pressure of the container 22, from an atmospheric level to that corresponding to the hospital pressurized system, simply by connecting the first feed opening 32 to a high pressure source of air propellant through the high pressure duct 3.

The container 22 is apt to house a bag M, wherefrom the physiological solution is extracted, as it will be apparent from the following description.

The propelling system 2 comprises a fitting element 33, removably sealed through the rigid walls of the container 22, and in particular through the lid 25.

In fact, the lid 25 has an appropriately shaped opening 34, the fitting element 33 being placed inside the latter.

The fitting element 33 has downwardly pair of side juttings 35 forming a bayonet joint with the opening 34.

For this purpose the fitting element 33 is embodied in elastically deformable material. The reciprocal sizes of the opening 34 and of the juttings 35 are such that the element 33 is forced internally to the opening 34 and rotated with interference among the surfaces of the element 33 and the lid 25 so as to obtain the required seal.

The fitting element 33 has an outer joint 36, apt to be connected to the delivery hose 5, and an inner joint 37 projecting, once the lid 25 is sealed, inside the container 22. Between the joints 36, 37 the element 33 has a through hole 38 connecting the inside of the container 22 with the outside thereof.

Externally to the lid 25, the fitting element further comprises a cylindrical surface 39 essentially knurled, apt to be handled by an operator.

The propelling system 2 comprises a piercing delivery element, which projects internally to the container 22 from said inner joint 37, comprising a fissured nose 41.

In the present embodiment, the piercing delivery element consists of a rigid tube 40 of plastic material that is forcibly engaged onto inner joint 37.

The rigid tube 40 presenting onto its inner end said fissured nose 41, comprising three fissures placed at 120° with respect to each other suited to pierce the flexible bag M once the lid 25 is sealed.

For this purpose, the rigid tube 40 extends for a length sufficient to interfere with the bag M, regardless of how the latter is positioned the inside the container 22.

Moreover, the rigid tube 40 is essentially S-shaped, so that the nose 41 has an essentially perpendicular incidence onto the flexible bag M when the lid 25 is closed, thereby facilitating the piercing of the same bag.

The propelling system 2 comprises discharge means 42 of pressure in excess inside the container 22. Such means 42 comprise a second feed opening 43, opened in the container 22, whereto a downcomer 44 fitted of a release valve 45 of the manually operated kind is connectible.

To the downcomer 44, also a control manometer 46 is connectable.

Once the bag M is placed into the container 22, the connections of the abovementioned ducts performed, the lid hermetically sealed and lastly the high pressure duct connected with the feed opening 32 and the suction hose directly to the suction duct 10 of the terminal element 4, the device 1 is ready for its activation.

In fact, it suffices to draw the terminal element 4 near to the area undergoing surgery to suck up, while removing the element it is possible to irrigate the area with the physiological solution of the bag M operating directly on the trigger 16.

The opening of the throttled tubule 14 allows the bag M to be compressed, causing spraying of the solution, by pressure gradient between the inside of the container 22 and the nozzle 12.

To check the supply, it suffices to release the trigger 16.

The abovementioned pressure gradient remains essentially constant until the emptying of bag M. Then it is possible to proceed to the replacement of the bag M, interrupting the circuit in pressure, discharging the container 22 internal pressure through the valve 44 and opening the lid 25.

Now, it suffices to remove the exhausted bag, place a full bag and close the lid 25.

The second bag is automatically pierced and, after having reconnected the circuit in pressure, it is possible to perform the irrigation.

Once surgery has ended, the replacement of components wet by the solution or by other organic fluids is carried on. They are: the terminal element 4 in its whole; the feed duct 5; the rigid tube 40 and the fitting element 33, all components of ready and easy replacement.

The above described surgical device 1 is subject to variants anyhow comprised in the scope of the present invention.

In particular, the piercing delivery element can comprise a hose, instead of said rigid tube 40, to implant manually into the bag M. Otherwise, said element can comprise only the fissured nose directly assembled on the fitting element inner joint.

The sizes of the fissured nose fissures can be varied to obtain a different flow rate of the physiological solution. Further, it is possible to provide a set of noses with different fissures to satisfy a broad range of surgical needs.

Beside the abovementioned advantage, the surgical device according to the invention has no parts in motion and is therefore more reliable.

Moreover, the construction of the device is considerably simple, allowing an easy functioning and a fast installation, and of cost-effective embeding.

The placement of the fitting, element and of the piercing element on the lid enables to pierce with great ease, and once the lid is sealed, the bag of solution, with no discharges inside the container.

The force to exert to pierce the bag is easily obtained thanks to the leverage determined by the lid rotating around the respective hinge.

Furthermore, replacement components are easily sterylisable or replaceable at a low cost.

To the abovedescribed surgical device of irrigation and suction a man skilled in the art, in order to satisfy further and contingent needs, may introduce several further modifications and variants, all however comprised in the protective scope of the present invention.

What is claimed is:

1. Surgical device (1) of irrigation and suction of a physiological solution extracted from a flexible bag (M), comprising a terminal element (4) of irrigation and suction, a propelling system (2) of the physiological solution, at least one delivery duct (5) connecting the propelling system (2) to the terminal element (4), wherein the propelling system (2) comprises:

a rigid wall container (22), adapted to house a sealed flexible bag (M), having an access side (23), a sealed lid (25), a feed opening (32) connectible to a high pressure source (3) of propellant fluid;

a fitting element (33), removably sealed through the lid (25) of the container (22), having a through hole (38) extended between an outer joint (36), for the connection of said delivery duct (5) and an inner joint (37) projecting inside the container (22) and;

a delivery element projecting inside the container (22) from said inner joint (37), wherein said delivery element is a piercing delivery element, (40, 41) having a fissured nose (41) adapted to pierce the sealed flexible bag (M) when the lid (25) is closed on the container.

2. Surgical device (1) according to claim 1, wherein the container (22) has cylindrical shape, said access side (23) being formed on a top side and being delimited by a round rim (24) cooperating with a grommet (27) of the lid (25).

3. Surgical device (1) according to claim 2, wherein the lid (25) is rotarably connected to a round rim (24) of the access side (23) by a hinge (26).

4. Surgical device (1) according to claim 2, wherein the coLitaine=(22) cowrprises blocking and sealing means (28) of the lid (25) to tote round rim (24).

5. Surgical device (1) according to claim 4, wherein the blocking and sealing means (28) are of the locking lever type.

6. Surgical device (1) according to claim 1, wherein the fitting element (33) is apt to be placed in an opening (34) into the rigid walls (25) of the container (22) appropriately shaped and has side jutting eleraents (35) forming a bayonet joint with said opening (34).

7. Surgical device (1) according to claim 6, wherein the side jutting elements (35) are elastically deformable and are apt, operating in a bayonet joint, to be forced in interference into the onening (34) to substantially obtain a seal between the rigid wall (25) of the container (22) and the fitting elemenet (33).

8. Surgical device (1) according to claim 6, wherein the fitting element (33) has, externally to the container (22), a cylindrical surface (39) essentially knurled.

9. Surgical device (1) according to claim 1, wherein said delivery element (40, 41) comprises a rigid tube (40) that is forcibly engaged on the inner joint (37), having on an inner end thereof said fissured nose (41), and extending for a length sufficient to interfere with the bag (M).

10. Surgical device (1) according to claim 1, wherein the fitting element (33) is removably sealed through the lid (25) of the container (22).

11. Surgical device (1) according to claim 9, wherein the rigid tube (40) is essentially S-shaped, the fissured nose (41) having an incidence essentially perpendicular to the flexible bag (M) with the lid (25) sealed.

* * * * *